United States Patent [19]
Mizukami et al.

[11] Patent Number: 5,719,179
[45] Date of Patent: Feb. 17, 1998

[54] COMPOUND GEX1

[75] Inventors: Tamio Mizukami; Yasushi Sakai; Tetsuo Yoshida; Youichi Uosaki, all of Machida; Keiko Ochiai, Ebina; Shiro Akinaga, Shizuoka, all of Japan

[73] Assignee: Kyowa Hakko Kogyo Co., Ltd., Tokyo, Japan

[21] Appl. No.: 772,941

[22] Filed: Dec. 24, 1996

[30] Foreign Application Priority Data

Dec. 28, 1995 [JP] Japan ................... 7-343702

[51] Int. Cl.$^6$ ............... C07D 407/04; C07D 407/14; A61K 31/35
[52] U.S. Cl. ................ 514/451; 549/414; 549/415; 514/460
[58] Field of Search ................ 549/414, 415; 514/451, 460

[56] References Cited

FOREIGN PATENT DOCUMENTS 06022770  2/1994  Japan .

OTHER PUBLICATIONS

The Journal of Antibiotics, vol. 45, No. 6 (Jun. 1992) 914–921.
Journal of Organic Chemistry, vol. 57, No. 26 (Dec. 18, 1992) 7720–26.
Synthesis, vol. 1996, No. 5 (May, 1996) 652–66.

*Primary Examiner*—Johann Richter
*Assistant Examiner*—Laura L. Stockton
*Attorney, Agent, or Firm*—Fitzpatrick, Cella, Harper & Scinto

[57]  ABSTRACT

Disclosed is Compound GEX1 of formula (I), having excellent antitumor activity:

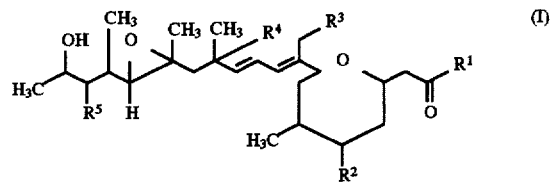

wherein $R^1$ represents hydroxy or

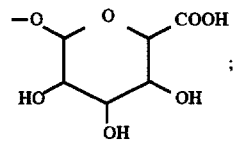

$R^2$, $R^3$ and $R^4$ independently represent hydrogen or hydroxy; $R^5$ represents hydroxyl or lower alkoxy; provided that when $R^1$ is hydroxy and $R^5$ is methoxy, then at least one of $R^2$, $R^3$ and $R^4$ is the group except for hydrogen, and pharmaceutically acceptable salts thereof.

3 Claims, No Drawings

COMPOUND GEX1

BACKGROUND OF THE INVENTION

The present invention relates to Compound GEX1 which has antitumor effect, and, therefore, is useful as antitumor agent.

TAN-1609 which is represented by formula (II):

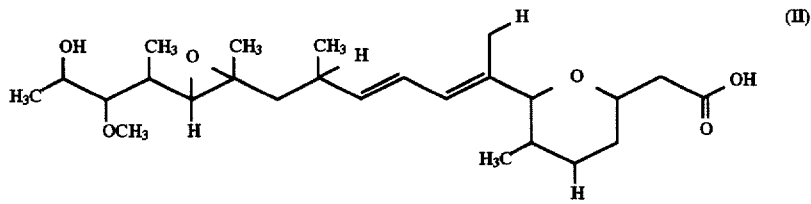

(II)

and which has antitumor activity (JP,A, 6-22770), and Herboxidiene [Journal of Antibiotics, 45, 914–921, (1992)] are known.

SUMMARY OF THE INVENTION

The present invention provides compounds having excellent antitumor activity.

Specifically, the present invention provides Compound GEX1 of formula (I):

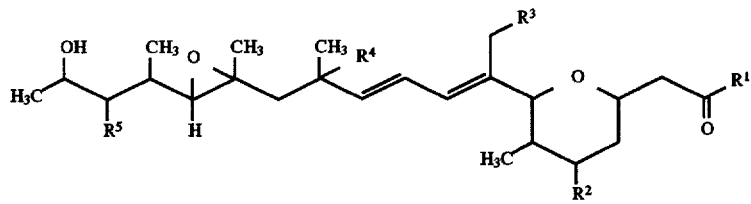

(I)

wherein $R^1$ represents hydroxy or

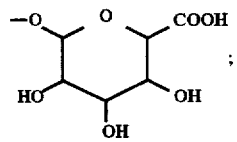

;

$R^2$, $R^3$ and $R^4$ independently represent hydrogen or hydroxy; $R^5$ represents hydroxyl or lower alkoxy; provided that when $R^1$ is hydroxy and $R^5$ is methoxy, then at least one of $R^2$, $R^3$ and $R^4$ is the group except for hydrogen, and pharmaceutically acceptable salts thereof.

The pharmaceutically acceptable salts of Compound GEX1 include pharmaceutically acceptable metal salts and ammonius salts.

Examples of the pharmaceutically acceptable metal salts are alkali metal salts such as sodium salt and pottasium salt and alkaline earth metal salts such as magnesium salt and calcium salt Examples of the pharmaceutically acceptable ammonium salts are ammonium salt and tetramethyl ammonium salt.

The present invention is described in detail below.

DETAILED DESCRIPTION OF THE INVENTION

In the definitions of the groups in formula (I), the lower alkoxy means a straight-chain or branched alkoxy group having 1 to 6 carbon atoms such as methoxy, ethoxy, n-propoxy, isopropoxy, butoxy, isobutoxy, sec-butoxy, tert-butoxy, pentyloxy, isoamyloxy and hexyloxy. Among Compounds GEX1 represented by formula (I), the compound wherein $R^1$ and $R^2$ are hydroxy, $R^3$ and $R^4$ are hydrogen, and $R^5$ is methoxy is referred to as GEX1Q1; the compound wherein $R^1$ and $R^4$ are hydroxy, $R^2$ and $R^3$ are hydrogen, and $R^5$ is methoxy is referred to as GEX1Q2; the compound wherein $R^1$ is

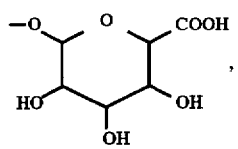

$R^2$, $R^3$ and $R^4$ are hydrogen, and $R^5$ is methoxy is referred to as GEX1Q3; the compound wherein $R^1$ and $R^3$ are hydroxyl groups, $R^2$ and $R^4$ are hydrogen atom, and $R^5$ is a methoxy group is referred to as GEX1Q4; and the compound wherein $R^1$ and $R^5$ are hydroxy, and $R^2$, $R^3$ and $R^4$ are hydrogen is referred to as GEX1Q5.

The physicochemical properties of Compound GEX1 are shown below. The apparatus used for measuring these are also shown below.

Melting point: Micro Melting Point Apparatus (Yanaco) Specific rotation: DIP-370 Digital Polarimeter (Jasco Corporation) FAB mass spectrum, and high-resolution FAB mass spectrum: JMS-HX110/110A Mass Spectrometer, (Jeol, Ltd.) absorption spectrum: UV-2200 Spectrophotometer (Shimadzu Corporation) IR absorption spectrum: JIR-RFX3001 Spectrophotometer (Jeol, Ltd.) $^{13}$C NMR and $^1$H NMR spectra: JNM-α400 NMR Spectrometer (Jeol, Ltd.), AM500 NMR Spectrometer (Bruker)

Physicochemical Data of GEX1Q1

Appearance: colorless oily solid Specific rotation: $[\alpha]_D^{25}=-13.5°$ (C=0.13, CH$_3$OH) Molecular formula: $C_{25}H_{42}O_7$ FAB mass spectrum (negative mode): m/z 453 (M—H)$^-$ High-resolution FAB mass spectrum (negative mode): m/z 453.2825 (M—H)$^-$Δ–2.7 mmu (as $C_{25}H_{42}O_7$— H) UV absorption spectrum: λmax(CH$_3$OH) nm (ε) 237 (26,400) IR absorption spectrum: vmax (KBr) cm$^{-1}$: 3700–2400, 3454, 1728, 1456, 1396, 1385, 1205, 1144, 1088, 1043, 970, 903, 887, 793, 648

$^{13}$C NMR spectrum (125 MHz, CD$_3$OD): δppm (multiplicity) 174.84 (s), 141.27 (d), 135.27 (s), 130.06

(d), 126.44 (d), 89.60 (d), 88.53 (d), 74.01 (d), 73.40 (d), 69.90 (d), 67.84 (d), 62.60 (s), 61.86 (q), 48.08 (t), 42.02 (t), 41.79 (d), 41.71 (t), 36.48 (d), 36.44 (d), 22.65 (q), 19.83 (q), 16.80 (q), 13.53 (q), 11.96 (q), 11.59 (q)

$^1$H NMR spectrum (500 MHz, $CD_3OD$): δppm (integration, multiplicity, coupling constant J (Hz)) 6.30 (1H, dd, 15.0, 10.8), 5.92 (1H, d, 10.8), 5.48 (1H, dd, 15.0, 9.0), 3.84 (1H, m), 3.78 (1H, dq, 6.2, 6.4), 3.52 (3H, s), 3.38 (1H, d, 10.0), 3.34 (1H, m), 2.97 (1H, dd, 6.2, 4.2), 2.65 (1H, d, 9.4), 2.50 (1H, dd, 15.4, 7.3), 2.45 (1H, m), 2.41 (1H, dd, 15.4, 5.7), 2.00 (1H, m), 1.91 (1H, dd, 13.5, 4.3), 1.69 (3H, d, 1.2), 1.50 (1H, ddq, 9.4, 4.2, 7.0), 1.41 (1H, m), 1.282 (1H, m), 1.276 (3H, s), 1.19 (1H, dd, 13.5, 10.9), 1.11 (3H, d, 6.4), 1.04 (3H, d, 6.7), 0.84 (3H, d, 7.0), 0.80 (3H, d, 6.6)

Solubility:

Soluble in methanol and dimethylsulfoxide (DMSO), but hardly soluble in hexane and chloroform.

Color reaction:

Positive to iodine staining reagent, sulfuric acid-ethanol staining reagent and phosphomolybdic acid/cerium sulfate staining reagent.

Thin layer chromatography: Rf 0.2

Thin layer: silica gel TLC (HPTLC plate Art. 15647, manufactured by Merck Co.) Developing solvent: methanol: chloroform=1:9 (v/v)

Physicochemical Data of GEX1Q2

Appearance: colorless oily solid Specific rotation: $[\alpha]_D^{25}$= +1.5° (C=0.128, $CH_3OH$) Molecular formula: $C_{25}H_{42}O_7$ FAB mass spectrum (negative mode): m/z 453 (M—H)$^-$ High-resolution FAB mass spectrum (negative mode): m/z 453.2868 (M—H)$^-$Δ+1.6 mmu (as $C_{25}H_{42}O_7$—H) UV absorption spectrum: λmax($CH_3OH$) nm (ε) 238 (26,600) IR absorption spectrum: νmax(KBr) $cm^{-1}$: 3700–2400, 3444, 1724, 1456, 1385, 1200, 1155, 1092, 1068, 1018, 972, 903

$^{13}$C NMR spectrum (100 MHz, $CD_3OD$): δppm (multiplicity) 175.14 (s), 141.33 (d), 137.37 (s), 129.24 (d), 124.12 (d), 92.09 (d), 88.56 (d), 75.49 (d), 73.26 (s), 69.91 (d), 67.82 (d), 62.12 (s), 61.87 (q), 51.82 (t), 42.30 (t), 36.38 (d), 33.47 (t), 33.45 (d), 32.79 (t), 30.79 (q), 19.84 (q), 18.72 (q), 18.09 (q), 12.28 (q), 11.58 (q)

$^1$H NMR spectrum (400 MHz, $CD_3OD$): δppm (integration, multiplicity, coupling constant J (Hz)) 6.52 (1H, dd, 15.4, 10.9), 5.98 (1H, dq, 10.9, 1.2), 5.74 (1H, d, 15.4), 3.79 (1H, dq, 6.2, 6.6), 3.76 (1H, m), 3.52 (3H, s), 3.36 (1H, d, 9.8), 2.97 (1H, dd, 6.2, 4.3), 2.74 (1H, d, 9.5), 2.46 (1H, dd, 15.3, 7.2), 2.38 (1H, dd, 15.3, 5.7), 2.14 (1H, d,. 14.2), 1.86 (1H, m), 1.73 (3H, d, 1.2), 1.70 (1H, m), 1.55 (1H, m), 1.52 (1H, m), 1.47 (1H, d, 14.2), 1.340 (1H, m), 1.339 (3H, s), 1.30 (3H, s), 1.26 (1H, m), 1.11 (3H, d, 6.6), 0.87 (3H, d, 7.1), 0.69 (3H, d, 6.6)

Solubility:

Soluble in methanol and dimethylsulfoxide (DMSO), but hardly soluble in hexane and chloroform.

Color reaction:

Positive to iodine staining reagent, sulfuric acid-ethanol staining reagent and phosphomolybdic acid/cerium sulfate staining reagent.

Thin layer chromatography: Rf 0.4

Thin layer: silica gel TLC (HPTLC plate Art. 15647, manufactured by Merck Co.) Developing solvent: methanol: chloroform=1:9 (v/v)

Physicochemical Data of GEX1Q3

Appearance: white, amorphous solid Melting point: 97.0°–98.0° C. Specific rotation: $[\alpha]_D^{26}$=+3.4° (C=0.115, $H_2O$) Molecular formula: $C_{31}H_{50}O_{12}$ FAB mass spectrum (negative mode): m/z 613 (M—H)$^-$ High-resolution FAB mass spectrum (negative mode): m/z 613.3214 (M—H)$^-$ Δ–1.1 mmu (as $C_{31}H_{50}O_{12}$—H) UV absorption spectrum: λmax($H_2O$) nm (ε) 238 (24,100) IR absorption spectrum: νmax(KBr) $cm^{-1}$: 3700–2400, 3419, 1749, 1716, 1456, 1385, 1084, 1059, 1018, 968

$^{13}$C NMR spectrum (125 MHz, $D_2O$): δppm (multiplicity) 173.41 (s), 172.66 (s), 141.24 (d), 135.14 (s), 130.47 (d), 126.36 (d), 94.49 (d), 91.96 (d), 88.30 (d), 76.30 (d), 75.85 (d), 74.99 (d), 72.44 (d), 71.94 (d), 69.61 (d), 68.71 (d), 65.23 (s), 62.09 (q), 46.80 (t), 41.22 (t), 35.61 (d), 35.49 (d), 32.38 (d), 32.29 (t), 31.67 (t), 22.23 (q), 19.26 (q), 17.68 (q), 16.04 (q), 12.30 (q), 10.88 (q)

$^1$H NMR spectrum (500 MHz, $D_2O$): δppm (integration, multiplicity, coupling constant J (Hz)) 6.43 (1H, dd, 15.2, 10.8), 6.09 (1H, d, 10.8), 5.65 (1H, d, 8.0), 5.64 (1H, dd, 15.2, 9.4), 4.08 (1H, m), 3.97 (1H, m), 3.89 (1H, dq, 6.8, 6.5), 3.65 (1H, m), 3.64 (1H, m), 3.58 (3H, s), 3.56 (1H, m), 3.54 (1H, d, 10.0), 3.10 (1H, dd, 6.8, 3.8), 2.95 (1H, d, 9.5), 2.73 (2H, m), 2.55 (1H, m), 2.11 (1H, dd, 13.3, 4.1), 1.92 (1H, m), 1.76 (1H, m), 1.74 (3H, d, 0.7), 1.68 (1H, m), 1.60 (1H, m), 1.48 (1H, m), 1.39 (3H, s), 1.33 (1H, m), 1.23 (1H, m), 1.17 (3H, d, 6.5), 1.08 (3H, d, 6.7), 0.85 (3H, d, 7.0), 0.73 (3H, d, 6.6)

Solubility:

Soluble in water, methanol and dimethylsulfoxide (DMSO), but hardly soluble in hexane and chloroform.

Color reaction:

Positive to iodine staining reagent, sulfuric acid-ethanol staining reagent and phosphomolybdic acid/cerium sulfate staining reagent.

Thin layer chromatography: Rf 0.5

Thin layer: ODS TLC (HPTLC plate Art. 15685, manufactured by Merck Co.) Developing solvent: methanol: water=6:4 (v/v)

Physicochemical Data of GEX1Q4

Appearance: colorless oily solid Specific rotation: $[\alpha]_D^{29}$= –4.9° (C=0.128, $CH_3OH$) Molecular formula: $C_{25}H_{42}O_7$ FAB mass spectrum (negative mode): m/z 453 (M—H)$^-$ High-resolution FAB mass spectrum (negative mode): m/z 453.2843 (M—H)$^-$Δ–1.0 mmu (as $C_{25}H_{42}O_7$—H) UV absorption spectrum: λmax($CH_3OH$) nm (ε) 238 (35,100) IR absorption spectrum: νmax(KBr) $cm^{-1}$: 3700–2400, 3444, 1716, 1456, 1385, 1200, 1153, 1086, 1066, 1014, 968, 904, 795

$^{13}$C NMR spectrum (125 MHz, $CD_3OD$): δppm (multiplicity) 175.09 (s), 143.04 (d), 137.85 (s), 132.95 (d), 125.97 (d), 90.51 (d), 88.52 (d), 75.77 (d), 69.91 (d), 67.77 (d), 62.54 (s), 61.85 (q), 58.34 (t), 47.87 (t), 42.32 (t), 36.35 (d), 36.27 (d), 34.22 (d), 33.57 (t), 32.70 (t), 22.30 (q), 19.83 (q), 18.33 (q), 16.79 (q), 11.56 (q)

$^1$H NMR spectrum (500 MHz, $CD_3OD$): δppm (integration, multiplicity, coupling constant J (Hz)) 6.48 (1H, dd, 14.8, 11.0), 6.04 (1H, d, 11.0), 5.62 (1H, dd, 14.8, 8.8), 4.22 (1H, ABq, 12.2), 4.18 (1H, ABq, 12.2), 3.79 (1H, dq, 6.4, 6.4), 3.76 (1H, m), 3.52 (3H, s),3.51 (1H, d, 10.5), 2.98 (1H, dd, 6.4, 4.2),2.65 (1H, d, 9.5), 2.48 (1H, m), 2.43 (2H, m), 1.89 (1H, dd, 13.5, 4.8), 1.88 (1H, m), 1.70 (1H, m), 1.63 (1H, m), 1.50 (1H, ddq, 9.5, 4.2, 7.0), 1.39 (1H, m) 1.282 (1H, m), 1.276 (3H, s), 1.24 (1H, dd, 13.5, 10.5),1.10 (3H, d, 6.4),1.06 (3H, d, 6.7),0.84 (3H, d, 7.0), 0.74 (3H, d, 6.6)

Solubility:

Soluble in methanol and dimethylsulfoxide (DMSO), but hardly soluble in hexane and chloroform.

Color reaction:

Positive to iodine staining reagent, sulfuric acid-ethanol staining reagent and phosphomolybdic acid/cerium sulfate staining reagent.

Thin layer chromatography: Rf 0.5

Thin layer: silica gel TLC (HPTLC plate Art. 15647, manufactured by Merck Co.) Developing solvent: methanol:chloroform=1:9 (v/v)

Physicochemical Data of GEX1Q5

Appearance: white powder Melting point: 114.0°–116.0° C.
Specific rotation: $[\alpha]_D^{29}=+14.6°$ (C=0.11, $CH_3OH$)
Molecular formula: $C_{24}H_{40}O_6$ FAB mass spectrum (negative mode): m/z 423 (M—H)⁻ High-resolution FAB mass spectrum (negative mode): m/z 423.2750 (M—H)⁻ Δ+0.4 mmu (as $C_{24}H_{40}O_6$—H) UV absorption spectrum: λmax($CH_3OH$) nm (ε) 237 (27,700) IR absorption spectrum: vmax(KBr) $cm^{-1}$ 3700–2400, 3365, 1716, 1456, 1194, 1072, 968, 912, 802, 694, 656, 582, 530

$^{13}C$ NMR spectrum (125 MHz, $CD_3OD$): δppm (multiplicity) 175.13 (s), 140.67 (d), 136.16 (s), 129.60 (d), 126.48 (d), 92.14 (d), 78.21 (d), 75.47 (d), 69.55 (d), 67.78 (d), 62.16 (s), 48.06 (t), 42.30 (t), 37.10 (d), 36.41 (d), 33.46 (t), 33.41 (d), 32.79 (t), 22.61 (q), 19.61 (q), 18.08 (q), 16.81 (q), 12.14 (q), 11.86 (q)

$^1H$ NMR spectrum (500 MHz, $CD_3OD$): δppm (integration, multiplicity, coupling constant J (Hz)) 6.30 (1H, dd, 15.0, 10.7), 5.91 (1H, d, 10.7), 5.48 (1H, dd, 15.0, 9.0), 3.77 (1H, dq, 5.3, 6.4), 3.76 (1H, m), 3.34 (1H, d, 9.9), 3.27 (1H, t, 5.2), 2.67 (1H, d, 9.4), 2.46 (1H, dd, 15.3, 7.3), 2.45 (1H, m), 2.38 (1H, dd, 15.3, 5.7), 1.89 (1H, dd, 13.4, 4.5), 1.85 (1H, m), 1.70 (1H, m), 1.69 (3H, d, 1.2), 1.54 (1H, m), 1.46 (1H, ddq, 9.4, 5.1, 7.0), 1.33 (1H, m), 1.29 (3H, s), 1.25 (1H, m), 1.18 (1H, dd, 13.4, 10.7), 1.12 (3H, d, 6.4), 1.04 (3H, d, 6.7), 0.87 (3H, d, 7.0), 0.68 (3H, d, 6.7)

Solubility:

Soluble in methanol and dimethylsulfoxide (DMSO), but hardly soluble in hexane.

Color reaction:

Positive to iodine staining reagent, sulfuric acid-ethanol staining reagent and phosphomolybdic acid/cerium sulfate staining reagent.

Thin layer chromatography: Rf 0.4

Thin layer: silica gel TLC (HPTLC plate Art. 15647, manufactured by Merck Co.) Developing solvent: methanol:chloroform=1:9 (v/v)

The biological activity of Compound GEX1 is described below, with reference to the following Test Example.

Test Example

Growth Inhibition against Human Epidermic Cancer A431 Cells

Human Epidermic Cancer A431 cells were put into a 96-well microtiter plate (Nunc #167008) at $3\times10^3$ cells/well, and cultured in a 5% $CO_2$ incubator at 37° C. for 24 hours. Each of 3 µg/ml GEX1 compounds was stepwise diluted. Each dilution was put into each well in an amount of 50 µl. The final concentration of the resulting suspension, in the wells of the plate was controlled to be at most 1 µg/ml. The cells were further cultured in the 5% $CO_2$ incubator at 37° C. for 72 hours. Five hours before the termination of the incubation, MTT [3-(4,5-dimethylthiazo-2-yl)-2,5-diphenyltetrazolium bromide, Sigma Co., St. Louis, Mo.] dissolved in a medium as used for the culturing was put into each well in an amount of 50 µl, the final concentration of MTT added in each well being 1 mg/ml. After the culturing, DMSO was added to each well in an amount of 150 µl, followed by vigorous stirring with a plate mixer to completely dissolve crystals of MTT-formazan. The absorbance at 550 nm was measured by using a microplate reader MTP-32 (Corona Electric Co., Ltd.). and the cell growth inhibiting activity of each GEX1 compound tested was expressed in terms of 50% growth inhibitory concentration ($IC_{50}$). The results are shown in Table 1.

TABLE 1

|  | $IC_{50}$ (µg/ml) A431 |
|---|---|
| GEX1Q1 | 0.42 |
| GEX1Q2 | 0.23 |
| GEX1Q3 | 0.020 |
| GEX1Q4 | 0.45 |
| GEX1Q5 | 0.0053 |

The process for producing Compound GEX1 is described below.

Compound GEX1 can be produced by culturing in a medium a microorganism belonging to the genus Streptomyces and having the ability to produce Compound GEX1, allowing Compound GEX1 to accumulate in the culture, and recovering Compound GEX1 from the culture.

As the GEX1-compound-producing strain, any strain may be employed so long as it belongs to the genus Streptomyces and has the ability to produce Compound GEX1. Alternatively, any mutant of such strain which is obtained by various artificial mutation methods such as UV irradiation, X-ray irradiation and treatment with mutagens, or by spontaneous mutation may be used in the present invention, so long as it is capable of producing Compound GEX1. A suitable example of such microorganisms is Streptomyces sp. GEX1 strain.

The present inventors have found that actinomycetes of GEX1 strain which were newly isolated from soil and which belong to the genus Streptomyces can produce Compound GEX1.

The morphological, cultural, physiological and chemotaxonomic characteristics of Streptomyces sp. GEX1 strain are described below.

1. Morphological Properties
1) Hyphae
Formation of aerial hyphae: Observed
Fragmentation and motility of aerial hyphae: Not observed
Fragmentation and motility of substrate hyphae: Not observed
2) Spores
Formation and location of spores:
Formed on the aerial hyphaehyphae
Formation and location of sporangia: Not observed
Number of spores in chain formed at the end of the sporophore: 10 or more.
Form of spore chains: Linear or flexuous
Characteristics of spores:
Surface; Smooth.
Form and size; Rods, about 0.4–0.7 µm×0.7–1.2 µm.
Motility and flagellum: Not observed
3) Others
Chlamydospores: Not observed
Synemata: Not observed
Pseudosporangia: Not obserbed
Branching Mode of Hyphae: Simple branching
2. Cultural characteristics The strain GEX1 shows moderate or good growth on synthetic and natural media which are generally used. The color of the substrate hyphae is pale yellow to brown. Formation of soluble brown pigment was observed on some of the culture media.

The following data show the growth and color characteristics of strain GEX1 observed after culturing the strain on various media at 28° C. for 14 days. The color names are given according to the Color Harmony Manual (Container Corporation of America, 4th Ed., 1958).

1) Sucrose-nitrate agar medium
   Growth: Good
   Color of substrate hyphae: Light olive gray (1½ ge)
   Formation and color of aerial hyphae:
   Abundant; white (a)—light olive gray (1½ ge)
   Soluble pigment: None 2) Glucose-asparagine agar medium
   Growth: Good
   Color of substrate hyphae:
   Oat meal (2 ec)—covert brown (2 nl)
   Formation and color of aerial hyphae:
   Abundant; parchment (1 cb)—mustard tan (2 lg)
   Soluble pigment: None 3) Glycerol-asparagine agar medium
   Growth: Good
   Color of substrate hyphae:
   Light olive gray (1½ ge)—mustard tan (2 lg)
   Formation and color of aerial hyphae:
   Abundant; white (a)—covert gray (2 fe)
   Soluble pigment: Formed (yellow)

4) Starch-inorganic salts agar medium
   Growth: Good
   Color of substrate hyphae:
   Mustard tan (2 lg)—dark brown (4 pn)
   Formation and color of aerial hyphae:
   Abundant; white (a)—citron gray (1 ge)
   Soluble pigment: Formed (brown)

5) Tyrosine agar medium
   Growth: Good
   Color of substrate hyphae:
   Covert tan (2 ge)—mustard tan (2 lg)
   Formation and color of aerial hyphae:
   Abundant; white (a)—patty (1 dc)
   Soluble pigment: None 6) Nutrient agar medium
   Growth: Poor
   Color of substrate hyphae: Bamboo (2 gc)
   Formation and color of aerial hyphae: Scant; white (a)
   Soluble pigment: None 7) Yeast malt agar medium
   Growth: Good
   Color of substrate hyphae:
   Bamboo (2 gc)—mustard brown (2 pl)
   Formation and color of aerial hyphae:
   Abundant; white (a) to patty (1 dc)
   Soluble pigment: Formed (yellow)

8) Oatmeal agar medium
   Growth: Good
   Color of substrate hyphae:
   Light olive (1½ ie)—mustard brown (2 ni)
   Formation and color of aerial hyphae:
   Abundant; white (a) to patty (1 dc)
   Soluble pigment: Formed (yellow)

3. Physiological characteristics:

The physiological characteristics of strain GEX1 are shown below. The result of 1) was obtained after 14 days of culturing and the results of 2) to 6) were obtained after 2 to 3 weeks of culturing at 28° C.

1) Growth temperature range: 8.0°–35.0° C.
2) Liquefaction of gelatin: Positive
3) Hydrolysis of starch: Positive
4) Coagulation and peptonization of skim milk powder: Negative
5) Production of melanin-like pigment
   (1) Peptone-yeast-iron agar medium: Negative
   (2) Tyrosine agar medium: Negative
6) Assimilability of carbon sources Pridham Gottlieb agar medium was used as the basal medium. In the following, "+" indicates that the strain utilized the carbon source, while "–" indicates that the strain did not utilize the carbon source.

L-arabinose: +
D-xylose: +
D-glucose: +
Sucrose: –
Raffinose: +
D-fructose: +
Rhamnose: +
Inositol: +
D-mannitol: +

4. Chemotaxonomic characteristics
1) Optical isomer of diaminopimelic acid in the strain: LL-form
2) Major quinone components of cellular lipid: MK-9($H_6$), MK-9($H_8$)

The strain is classified in the genus Streptomyces among actinomycetes in view of its characteristics: that spore chains are formed on the aerial hyphae; that it belongs to the Type I cell wall group (LL-diaminopimelic acid); and that the major quinone components are hexahydrogenated menaquinone 9 [MK-9($H_6$)] and octahydrogenated menaquinone 9 [MK-9 ($H_8$)].

The strain was named streptomyces sp. GEX1 and was deposited with the National Institute of Bioscience and Human-Technology, Agency of Industrial Science and Technology on Dec. 21, 1995 with the accession number FERM BP-5437 under the Budapest Treaty.

For culturing the microorganisms capable of producing Compound GEX1 of the present invention, conventional methods for culturing actinomycetes are generally employed. As the medium, either a synthetic medium or a natural medium may be used so long as it appropriately contains carbon sources, nitrogen sources and inorganic substances which can be assimilated by the strains employed, and the growth- and productions promoting substances required.

As the carbon sources, glucose, starch, dextrin, mannose, fructose, sucrose, lactose, xylose, arabinose, mannitol, molasses, etc. can be used singly or in combination. In addition, hydrocarbons, alcohols, and organic acids, etc. may also be used, depending on the assimilability of the microorganisms employed.

As the nitrogen sources, ammonium chloride, ammonium nitrate, ammonium sulfate, sodium nitrate, urea, peptone, meat extract, yeast extract, dry yeast, corn steep liquor, soybean meal, casamino acids, etc. can be used singly or in combination.

If necesssary, the medium may contain inorganic salts such as sodium chloride, potassium chloride, magnesium sulfate, calcium carbonate, potassium dihydrogen phosphate, ferrous sulfate, calcium chloride, magnesium sulfate, zinc sulfate, and copper sulfate. Further, trace ingredients that promote the growth of the strain employed and the production of Compound GEX1 may be optionally added to the medium.

In the culturing, liquid culture, especially submerged stirring culture is more preferably employed. The culturing is carried out at 16° to 37° C., preferably 25° to 32° C., at pH 4 to 10, preferably pH 6 to 8. In order to adjust the pH of the medium, aqueous ammonia, ammonium carbonate solution, etc. may be added to the medium. In general, culturing is completed in 1 to 7 days, and Compound GEX1 are produced and accumulated in the culture broth and microbial cells. When the amount of the product in the culture reaches the maximum, the incubation is discontinued.

The Compound GEX1 thus accumulated in the culture may be isolated and purified from the culture in accordance with the methods commonly employed for the isolation and purification of microbial metabolites from cultures. If desired, the compounds may be chemically modified for facilitating the isolation thereof.

For example, the culture is separated into culture filtrate and microbial cells by filtration. The microbial cells are extracted with a solvent such as chloroform or acetone. Then, the extract is mixed with the culture filtrate and rhw ewaulrinf mizruew ia passed through a column of polystyrene adsorbent such as Diaion HP-20 (manufactured by Mitsubishi Chemical Corporation) to adsorb the active substance, followed by elution with a solvent such as methanol and acetone. The eluate is concentrated, and the concentrate is subjected to ODS column chromatography, high performance liquid chromatography, silica gel column chromatography, etc. to give Compound GEX1. During the culture, isolation and purification steps, Compound GEX1 can be detected by using thin layer chromatography, and then by an iodine staining reagent.

Examples of the present invention are shown below.

EXAMPLE 1

Streptomyces sp. GEX1 strain was used as an inoculum.

The strain was inoculated into 300. ml of a seed medium (pH 7.2 before sterilization) having the following composition in a 2-liter Erlenmeyer flask, and cultured with shaking (rotation: 200 rpm) at 28° C. for 48 hours.

Composition of the seed medium: 10 g/liter glucose, 10 g/liter soluble starch, 5 g/liter Bacto Trypton (manufactured by Difco), 5 g/liter yeast extract, 3 g/liter meat extract, and 0.5 g/liter magnesium phosphate The seed culture thus obtained was transferred into 18 liters of a fermentation medium having the following composition in a 30-liter jar fermenter in an amount of 5% (by volume), and cultured with stirring and aeration (ratation: 250 rpm, aeration: 18 liters/min.) at 25° C.

Composition of Fermentation Medium: 50 g/liter soluble starch, 15 g/liter dry yeast, 0.5 g/liter $KH_2PO_4$, 0.5 g/liter of $Mg_3(PO_4)_2 \cdot 8H_2O$ (pH 7.0 before sterilization, adjusted with NaOH)

Culturing was carried out for 72 hours without controlling the pH of the medium. The resulting culture was separated into culture filtrate and microbial cells by filtration. The culture filtrate was passed through a column of Diaion HP-20 to adsorb the active substance. The impurities were eluted with methanol-water (3:7, v/v), and the active substance was eluted with acetone. The active fraction thus eluted was concentrated, and passed through a column of Diaion HP-20SS to adsorb the active substance. The impurities were eluted with 10 mM sodium acetate containing acetonitrile-water (2:8, v/v). Then, the active substance was eluted with 10 mM sodium acetate containing acetonitrile-water (3:7–5:5, v/v). The active fractions thus eluted were concentrated, and a fraction containing GEX1Q1 and GEX1Q3, and a fraction containing GEX1Q1, GEX1Q2, GEX1Q4 and GEX1Q5 were obtained. Each fraction was passed through an ODS column (ODS-AM 120-230/70, manufactured by YMC) to adsorb the active substance. The impurities were eluted with 10 mM sodium acetate containing acetonitrile-water (2:8, v/v). Then, the active substance was eluted with 10 mM sodium acetate containing acetonitrile-water (3:7, v/v) and 10 mM sodium acetate containing acetonitrile-water (4:6, v/v). The active fractions thus eluted were concentrated, and a fraction consisting essentially of GEX1Q1, a fraction consisting essentially of GEX1Q1, GEX1Q2 and GEX1Q4, a fraction consisting essentially of GEX1Q4, and a fraction consisting essentially of GEX1Q5 were obtained. The fractions were subjected to high performance liquid chromatography (HPLC) under the following conditions to obtain solutions of GEX1Q1, GEX1Q2, GEX1Q3, GEX1Q4 and GEX1Q5, separately. Each solution was concentrated and passed through a column of Diaion HP-20 to adsorb the active substance. The column was then washed with cold water and desalted, and the active substance was eluted with acetonitrile, and concentrated to dryness to give 46 mg of GEX1Q1, 87 mg of GEX1Q2, 8.3 mg of GEX1Q3, 73 mg of GEX1Q4, and 24 mg of GEX1Q5.

HPLC Conditions:

Column: ODS 120 A S-5 (SH343-5, manufactured by YMC)

Flow Rate: 10 ml/min.

Detection: 237 nm

Retention Time/Eluent:
  GEX1Q1: 20 min/acetonitrile-water (30:70, v/v) (containing 10 mM sodium acetate)
  GEX1Q2: 26 min/acetonitrile-water (30:70, v/v) (containing 10 mM sodium acetate)
  GEX1Q3: 33 min/acetonitrile-water (30:70, v/v) (containing 10 mM sodium acetate)
  GEX1Q4: 40 min/acetonitrile-water (30:70, v/v) (containing 10 mM sodium acetate)
  GEX1Q5: 50 min/acetonitrile-water (35:65, v/v) (containing 10 mM sodium acetate)

What is claimed is:

1. A compound of formula (I):

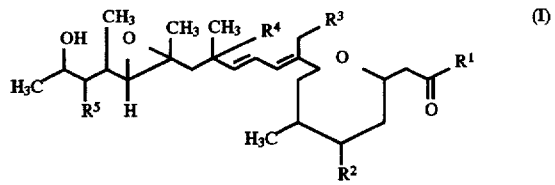

wherein $R^1$ represents hydroxy or

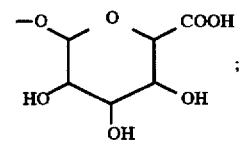

;

$R^2$, $R^3$ and $R^4$ independently represent hydrogen or hydroxy; $R^5$ represents hydroxyl or lower alkoxy; provided that when $R^1$ is hydroxy and $R^5$ is methoxy, then at least one of $R^2$, $R^3$ and $R^4$ is other than hydrogen, or pharmaceutically acceptable salts thereof.

2. A compound or a pharmaceutically-acceptable salt thereof as claimed in claim 1, which are any of a compound where $R^1$ and $R^2$ are hydroxyl groups, R3 and $R^4$ are hydrogen atoms, and $R^5$ is a methoxy group; a compound where $R^1$ and $R^4$ are hydroxyl groups, $R^2$ and $R^3$ are hydrogen atoms, and $R^5$ is a methoxy group; a compound where $R^1$ is a group of:

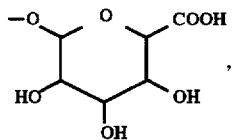

$R^2$, $R^3$ and $R^4$ are hydrogen atoms, and $R^5$ is a methoxy group; a compound where $R^1$ and $R^3$ are hydroxyl groups, $R^2$ and $R^4$ are hydrogen atoms, and $R^5$ is a methoxy group; a compound where $R^1$ and $R^5$ are hydroxyl groups, and $R^2$, $R^3$ and $R^4$ are hydrogen atoms; or a pharmaceutically-acceptable salt of said compounds.

3. A pharmaceutical composition comprising any of the compounds of claim 1 or 2, and a pharmaceutically-acceptable carrier or diluent.

* * * * *

UNITED STATES PATENT AND TRADEMARK OFFICE
CERTIFICATE OF CORRECTION

PATENT NO. : 5,719,179

DATED : February 17, 1998

INVENTOR(S) : TAMIO MIZUKAMI, ET AL.          Page 1 of 2

It is certified that error appears in the above-identified patent and that said Letters Patent is hereby corrected as shown below:

Title page,
AT [56] REFERENCES CITED

FOREIGN PATENT DOCUMENTS

"06022770" should read --6-022770--.

COLUMN 1

Line 5, "antitumor" should read --an antitumor-- (both occurrences);
Line 19, "antitumor" should read --an antitumor-- and "(JP,A," should read --(JP-A,--; and
Line 57, "pottasium" should read --potassium--.

COLUMN 2

Line 41, "atom," should read --atoms,--; and
Line 51, "absorption" should read --UV absorption--.

COLUMN 3

Line 7, "3,84" should read --3.84--;
Line 49, "1,73" should read --1.73--; and
Line 50, "1,47" should read --1.47--.

COLUMN 6

Line 47, "hyphaehyphae" should read --hyphae--;
Line 54, "Surface;" should read --Surface:--;
Line 55, "size;" should read --size:--; and
Line 60, "obserbed" should read --observed--.

UNITED STATES PATENT AND TRADEMARK OFFICE
CERTIFICATE OF CORRECTION

PATENT NO. : 5,719,179
DATED : February 17, 1998
INVENTOR(S) : TAMIO MIZUKAMI, ET AL.

It is certified that error appears in the above-identified patent and that said Letters Patent is hereby corrected as shown below:

COLUMN 8

Line 45, "productions promoting" should read --production-promoting--.

COLUMN 9

Line 6, "are" should read --is--;
Line 19, "rhw" should read --the--;
Line 20, "ewaulrinf mizruew ia" should read --resulting mixture is--; and
Line 47, "(ratation:" should read --(rotation:--.

COLUMN 10

Line 66, "R3" should read --$R^3$--.

Signed and Sealed this

Twenty-fifth Day of August, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,719,179
DATED : February 17, 1998
INVENTOR(S) : Tamio Mizukami et al.

It is certified that error appears in the above-identified patent and that said Letters Patent is hereby corrected as shown below:

Column 8,
Line 37, "BP-5437" should read -- BP-5347 --.

Signed and Sealed this

Fifteenth Day of November, 2005

JON W. DUDAS
*Director of the United States Patent and Trademark Office*